(12) United States Patent
Sun (10) Patent No.: US 11,833,358 B2
(45) Date of Patent: Dec. 5, 2023

(54) CARDIAC IMPLANTATION DEVICE AND PACING SYSTEM

(71) Applicant: MICROPORT SOARING CRM (SHANGHAI) CO., LTD., Shanghai (CN)

(72) Inventor: Jiangkai Sun, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/046,718

(22) PCT Filed: Apr. 10, 2019

(86) PCT No.: PCT/CN2019/081995
§ 371 (c)(1),
(2) Date: Oct. 9, 2020

(87) PCT Pub. No.: WO2019/196851
PCT Pub. Date: Oct. 17, 2019

(65) Prior Publication Data
US 2021/0162226 A1   Jun. 3, 2021

(30) Foreign Application Priority Data

Apr. 10, 2018 (CN) .......................... 201810316078.2

(51) Int. Cl.
*A61N 1/37* (2006.01)
*A61N 1/375* (2006.01)

(52) U.S. Cl.
CPC ....... *A61N 1/37518* (2017.08); *A61N 1/3756* (2013.01); *A61N 1/37512* (2017.08)

(58) Field of Classification Search
CPC ............ A61N 1/37518; A61N 1/37512; A61N 1/3756
See application file for complete search history.

(56) References Cited

U.S. PATENT DOCUMENTS

| 9,486,628 B2 * | 11/2016 | Christopherson .... A61N 1/0551 |
| 2011/0251660 A1 * | 10/2011 | Griswold ............. A61N 1/3756 607/126 |

(Continued)

FOREIGN PATENT DOCUMENTS

| CN | 1280475 A | 1/2007 |
| CN | 103328040 A | 9/2013 |

(Continued)

*Primary Examiner* — Eric D. Bertram
(74) *Attorney, Agent, or Firm* — Muncy, Geissler, Olds & Lowe, P.C.

(57) ABSTRACT

A medical device for treating cardiac rhythm disorders, and a cardiac implantation device and a pacing system. The cardiac implantation device includes: a first connecting member having an end configured to be coupled to a pacemaker; and N support struts, each of the N support struts having a proximal end coupled to the other end of the first connecting member. The support struts are provided thereon with anchor(s) configured to secure during implantation. Distal ends of the support struts are free and are able to radiate outwardly or converge inwardly. The pacing system includes the implantation device and a pacemaker. A leadless pacemaker can be implanted into the superior vena cava in order to achieve atrial sensing and pacing. Moreover, the leadless pacemaker can be more easily retrieved after long-term implantation at a high success rate, promoting the application of leadless pacemakers and enhancing patients' use experience.

10 Claims, 6 Drawing Sheets

(56) References Cited

U.S. PATENT DOCUMENTS

| | | | | |
|---|---|---|---|---|
| 2012/0172891 A1* | 7/2012 | Lee | ............ | A61N 1/3756 |
| | | | | 606/129 |
| 2013/0110208 A1* | 5/2013 | Inagaki | ............ | A61N 1/0551 |
| | | | | 607/116 |
| 2015/0306378 A1* | 10/2015 | Schmidt | ............ | A61N 1/3756 |
| | | | | 607/126 |
| 2017/0106185 A1* | 4/2017 | Orts | ............ | A61N 1/0573 |
| 2017/0151429 A1* | 6/2017 | Regnier | ............ | A61N 1/3756 |
| 2018/0126179 A1* | 5/2018 | Haasl | ............ | A61N 1/059 |
| 2020/0261715 A1* | 8/2020 | Eby | ............ | A61N 1/3756 |

FOREIGN PATENT DOCUMENTS

| | | |
|---|---|---|
| CN | 106362288 A | 2/2017 |
| CN | 106659898 A | 5/2017 |
| CN | 107106848 A | 8/2017 |
| CN | 107233665 A | 10/2017 |
| CN | 108310652 A | 7/2018 |
| EP | 3285866 | 10/2016 |
| EP | 2654889 B1 | 3/2017 |
| WO | WO-2015/017282 A1 | 2/2015 |

* cited by examiner

CARDIAC IMPLANTATION DEVICE AND PACING SYSTEM

TECHNICAL FIELD

The present invention relates to the technical field of cardiac rhythm medical equipment and, more particular, to a cardiac implantation device and a pacing system.

BACKGROUND

With the development of technology, leadless pacemakers are finding increasingly extensive use in clinical practice and are considered to have wider application in the future because they are free of various complications arising from the use of traditional pacemakers with leads.

However, the inventors have found that existing leadless pacemakers are at least associated with the following problems: in current surgery, the leadless pacemakers are mostly implanted in ventricles to sense ventricular events; and according to some reports, a retrieval success rate of such pacemakers after long-term implantation is about 91%. That is, leadless pacemakers whose service lives have expired cannot be 100% extracted, meaning that some patients have to carry two or more leadless pacemakers. So far, there has been no physical equipment, patent document or literature that can provide an effective solution for atrial pacing or for the problem of low long-term retrieval success rate.

SUMMARY OF THE INVENTION

It is an object of the present invention to provide a cardiac implantation device and a cardiac pacing system, which allow implantation of a leadless pacemaker into the superior vena cava so that the leadless pacemaker is capable of atrial sensing and pacing. Moreover, the leadless pacemaker can be more easily retrieved after long-term implantation at a high success rate, promoting the application of leadless pacemakers and enhancing patients' use experience.

The above object is attained by a cardiac implantation device according to an embodiment of the present invention, which comprises: a first connecting member having a proximal end configured to be coupled to a pacemaker; and N support struts, each of the N support struts having a proximal end coupled to a distal end of the first connecting member. At least one of the support struts is each provided with an anchor configured to secure the pacemaker during implantation. Each of the support struts has a distal end that is free and is able to radiate outwardly or converge inwardly. N is a natural number greater than or equal to 1.

In another embodiment, the anchor may have a needle tip-like structure or a barb-like structure.

In another embodiment, the anchor may be arranged at a distal end or on a middle section of the support strut.

In another embodiment, N may be greater than 1, and the proximal ends of the N support struts may be evenly arranged along a part of a circumference of a distal end portion of the first connecting member.

In another embodiment, the part of the circumference may be at least half the circumference.

In another embodiment, the N support struts may be coupled to the distal end of the first connecting member by welding or crimping.

In another embodiment, the cardiac implantation device may be made of a biocompatible metallic material, and the N support struts may be made of a biocompatible elastic metallic material.

The above object is also attained by a cardiac pacing system according to an embodiment of present invention, which comprises the cardiac implantation device as defined above and a pacemaker coupled to the cardiac implantation device.

In another embodiment, the first connecting member of the cardiac implantation device may be coupled, at the proximal end, to the pacemaker through a second connecting member.

In another embodiment, each of the first and second connecting members may have a cylinder-like structure, and the first and second connecting members are connectable with each other in a matching manner.

In another embodiment, the second connecting member may connect with the first connecting member in a matching manner by an internal or an external thread.

In another embodiment, an end of the pacemaker that is not coupled to the cardiac implantation device may be provided with a pull hook.

In another embodiment, prior to implantation of the cardiac pacing system, the N support struts of the cardiac implantation device may be received in a positioning sheath.

Compared with the prior art, the cardiac implantation device of the present invention can be better secured at a certain position of the superior vena cava, thus allowing easy implantation of a leadless pacemaker in the superior vena cava for pacing in the vicinity of the atrium. In this way, operation of the leadless pacemaker begins with atrial pacing, and a pacing signal then propagates from the atrium to the corresponding ventricle. This pacing sequence is close to patients' natural pacing sequence, and true physiological pacing can be thus achieved. The cardiac implantation device is simple in structure and easy to be secured, folded and extracted and thus allows easy implantation and retrieval of a leadless pacemaker. Further, the cardiac implantation device can be stably supported and secured in the superior vena cava, allowing stable positional maintenance of the leadless pacemaker at the target site. Furthermore, the N support struts are adapted to be firmly stuck on the vessel wall and allow satisfactory sensing and pacing. All of these can help in promoting the application of leadless pacemakers and enhancing patients' use experience.

BRIEF DESCRIPTION OF THE DRAWINGS

Exemplary description of one or more embodiments will be given below with reference to the corresponding accompanying drawings, but the embodiments are not limited to this description. Like reference numerals indicate similar or identical elements throughout the drawings, which are not necessarily drawn to scale, unless otherwise stated.

DETAILED DESCRIPTION

In order that the objects, subject matter and advantages of embodiments of the present invention may be more clearly understood, a number of embodiments of the invention will now be described with reference to the accompanying drawings. However, those of ordinary skill in the art will appreciate that although numerous technical details are set forth in the following description to provide reader with a better understanding of the present application, the subject matter sought to be protected in this application can be achieved without these technical details or based on various changes or modifications made to the embodiments disclosed hereinafter.

The terms "proximal" and "distal" will be used herein to describe relative orientations, relative positions or directions of components or actions with respect to one another, from the perspective of a physician using a medical instrument. While not meant to be limiting, a "proximal end" of the medical instrument generally refers to the end thereof that is located closer to the physician when in a normal operating state of the instrument, while a "distal end" of the instrument generally refers to the end thereof that enters the body of a patient first.

A first embodiment of the present invention relates to a cardiac implantation device 1, which, as shown in FIGS. 1 to 4, includes: a first connecting member 10, which can be coupled at a first (proximal) end to a pacemaker 2 (here, a leadless pacemaker); and N support struts 11, each of the N support struts having a proximal end coupled to a second (distal) end of the first connecting member 10. At least one of the support struts 11 is provided with an anchor 111 configured to secure the implantation device within the superior vena cava during implantation thereof. Here, each of the support struts 11 may be provided with such an anchor 111. The support struts 11 have respective free distal ends that will elastically yield to forces applied to the N support struts 11 and converge toward an axis of the first connecting member 10. When the forces are removed, the support struts 11 will again radiate away from the axis by their elasticity. N is a natural number greater than or equal to 1. The pacemaker 2 is preferably a leadless pacemaker. According to this embodiment, in a natural state of the cardiac implantation device, the N support struts 11 diverge and press against the inner wall of the superior vena cava, thus providing the leadless pacemaker 2 with stable support and securing it. Retrieval can be accomplished simply by separating the support struts 11 from the superior vena cava through applying inward forces to the support struts 11. In this way, the cardiac implantation device according to this embodiment allows a very high retrieval success rate of the leadless pacemaker. In addition, as the cardiac implantation device according to this embodiment enables implantation of the leadless pacemaker in the superior vena cava, sensing of atrial events and atrial pacing can be achieved, providing for true physiological pacing, which is helpful in promoting the application of leadless pacemakers and improving user experience. For the only purpose of facilitating an understanding, details in implementation of the cardiac implantation device according to this embodiment will be set forth below, which are, however, considered that the implementation can be made without one or more of these details.

In embodiments of the present invention, the N support struts 11 serve to support and secure the leadless pacemaker 2. That is, the N support struts can support the total weight of the leadless pacemaker 2 so that the implanted leadless pacemaker 2 will not experience any displacement. In different embodiments, the number N of the support struts 11 may vary depending on the actual needs, and is generally greater than 1, such as 4. In this embodiment, N is not limited to any particular value, as along as the N support struts 11 enable implantation of the leadless pacemaker 2 in a human vein.

Figure 5:
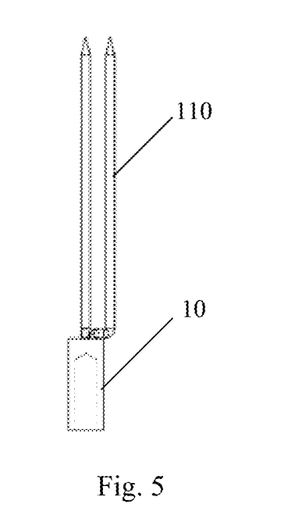
FIG. 5 is a schematic diagram illustrating a cardiac implantation device according to a second embodiment of the present invention in a folded configuration.

When N is greater than 1, the proximal ends of the N support struts may be evenly arranged along part of a distal end circumference of the first connecting member 10. In this way, the cardiac implantation device 1 can be implanted with more points of securing the pacemaker 2 to the superior vena cava, which enable more stable implantation of the leadless pacemaker 2 at the target site (i.e., the superior vena cava). In this embodiment, the four support struts 11 are evenly distributed along part of the end circumference of the first connecting member 10. In this way, in addition to stable implantation of the pacemaker 2, the forces applied to the superior vena cava can be maximally even, which can minimize damage to the wall of the superior vena cava. That is, safe implantation of the leadless pacemaker 2 can be achieved. In this embodiment, the part of the circumference may be greater than half the circumference. In this way, adjacent ones of the N support struts 11 may be spaced apart from each other at their respective ends with a relative large distance, thereby minimizing the impact on the blood flow in the superior vena cava. In this way, normal blood flow can be maintained within the superior vena cava subsequent to the implantation of the cardiac implantation device 1 and the pacemaker 2. In the example shown in FIG. 5, each of the four support struts 11 may be fixed at one end to half of the end circumference of the cylindrical first connecting member 10. In alternative examples, the N support struts 11 may be distributed in symmetry at the end of the first connecting member 10. This embodiment is not limited to any particular positions or distribution of the support struts 11 on the first connecting member 10. In embodiments of the present invention, the four support struts may be coupled to the other end of the first connecting member 10 by welding or crimping. This embodiment is not limited to any particular coupling between the support strut 11 and the first connecting member 10. In one example, the cardiac implantation device may be a unitary part made by 3D printing. This embodiment is not limited to any particular fabrication method of the cardiac implantation device 1.

Each support strut 11 may include a strut body 110 and the anchor 111 arranged at the distal end or a middle section of the strut body 110. In this embodiment, the strut body 110 may be integrated with the anchor 111. For example, the strut body 110 and anchor 111 may form an integral part made of a nickel-titanium alloy, allowing simple and low-cost fabrication. The anchor 111 may be arranged at the distal end of the strut body 110. This embodiment is not limited to any particular coupling, fabrication or positioning of the strut body 110 and the anchor 111.

The anchors 111 are configured to secure the cardiac implantation device 1 to the inner wall of the superior vena cava and allow easy attachment and detachment of the cardiac implantation device on and from the superior vena cava. Here, the "superior vena cava" is meant to refer to, without limitation, either a major part of the superior vena cava, or both the superior vena cava and the junction of the superior vena cava and the atrium. Each anchor 111 may be considered as a portion of the corresponding support strut 11, such as an end portion of the support strut 11 or a projection portion located at the end of the support strut 11. In the unfolded state of the support struts 11, the anchors 111 can abut against and engage with the inner wall of the superior vena cava, thereby supporting and securing the implanted pacemaker 2.

Preferably, the anchors 111 have a needle tip-like structure, which can better support and secure the implanted pacemaker 2 by piercing into the vessel inner wall and preventing the pacemaker 2 from dislodgement due to the beating of the heart. When the needle tip-like anchors 111 pierce into the inner wall of the superior vena cava, the N support struts 11 can provide securing support to the leadless pacemaker 2 in the cardiac implantation device 1. Specifically, the anchors 111 may be implemented as, for example, conical needle tips which can penetrate into the inner wall of the superior vena cava and stay therein when the strut bodies 110 abut thereon. The needle tip may have a length that allows reliable securing while not causing the needle tips to penetrate through the wall of the superior vena cava. This embodiment is limited to any particular shape or size of the needle tips.

The supporting and securing performance of the cardiac implantation device 1 may be a function of factors including the diameter, length, material strength, fabrication method and number of the strut bodies 110, the shape of the anchors 111 and the like. Accordingly, in practice, the design of the cardiac implantation device may take into amount these factors. This embodiment is not limited to any structural detail in the support struts 11.

Figure 1:
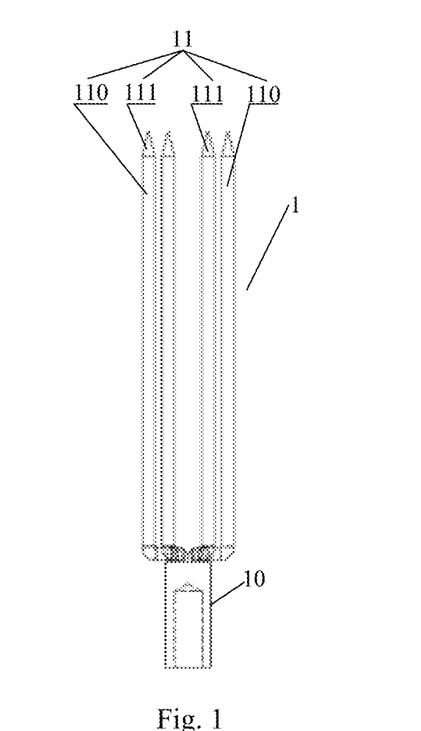
FIG. 1 is a schematic diagram illustrating a cardiac implantation device according to a first embodiment of the present invention in a folded configuration.
Figure 2:
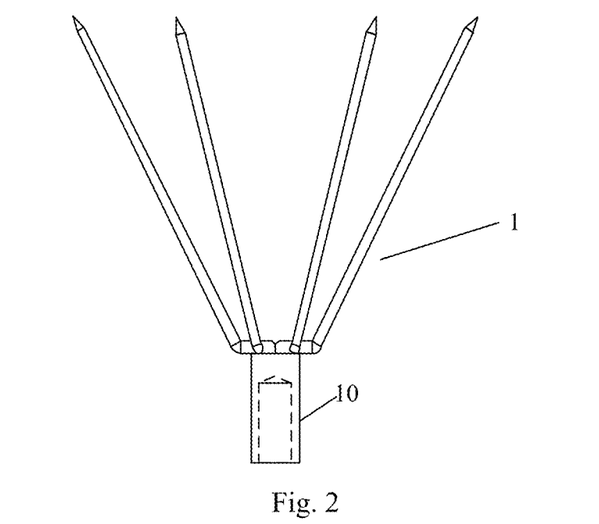
FIG. 2 is a schematic diagram illustrating the cardiac implantation device according to the first embodiment of the present invention in an unfolded configuration.
Figure 3:
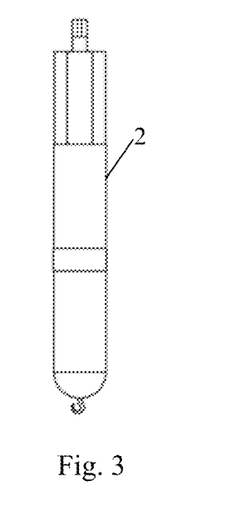
FIG. 3 is a structural schematic of a pacemaker that can be used with the cardiac implantation device according to the first embodiment of the present invention.
Figure 4:
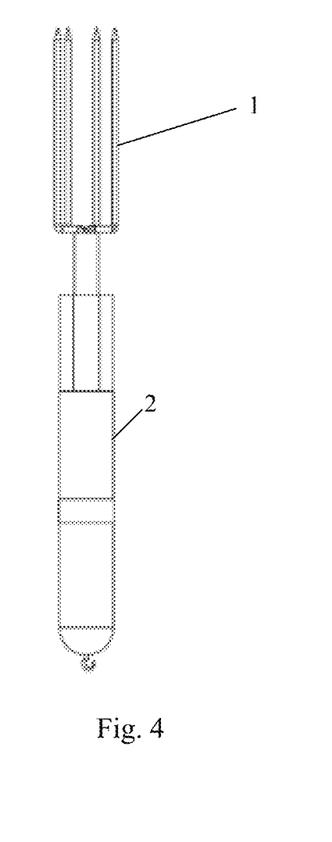
FIG. 4 schematically illustrates the coupling of first and second connecting members according to the first embodiment of the present invention to a leadless pacemaker.

FIG. 3 is a structural schematic of the leadless pacemaker 2, and FIG. 4 schematically illustrates how the cardiac implantation device 1 is used with the leadless pacemaker 2. The first connecting member 10 of the cardiac implantation device 1 may be coupled to the pacemaker 2 by a second connecting member, and the coupling may be accomplished threadedly. The second connecting member may be fixedly disposed on the pacemaker 2 and serve as a component of the pacemaker 2. Alternatively, the second connecting member may be detachably coupled to the pacemaker 2. For example, the second connecting member may be threadedly coupled to the pacemaker 2. In this case, the second connecting member may either serve as a component of the pacemaker 2 or as a standalone component. Specifically, the second connecting member may be coupled to the first connecting member 10 by an internal thread or an external thread. This embodiment is not limited to any particular position where the thread is formed in the second connecting member. This embodiment is also not limited to any particular form of the first 10 or second connecting member. Typically, these connecting members may be both cylindrical so as to be implanted into a blood vessel more easily.

In this embodiment, the implant may be made of biocompatible metallic material(s). For example, the first connecting member 10 may be made of MP35N which is a non-magnetic nickel-cobalt-chromium-molybdenum alloy featuring unique super high tensile strength, good ductility, toughness and superior corrosion resistance. The support struts 11 may be formed of a biocompatible elastic metallic material such as a nickel-titanium alloy. Of course, the support struts 11 may be alternatively made of any of other metallic materials with good biocompatibility and excellent elasticity, which will not bring damage to the human body. This embodiment is not limited to any of the materials listed above.

Figure 11:
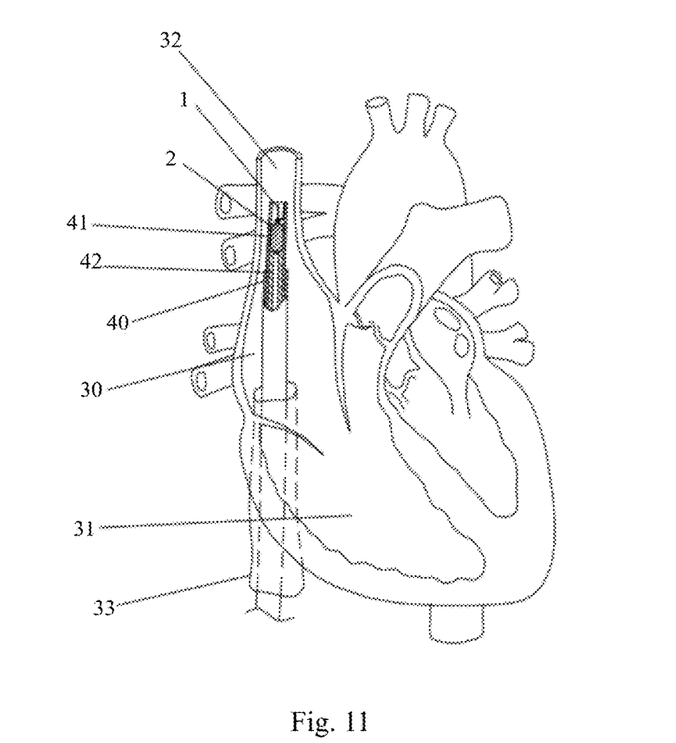

In this embodiment, when the N support struts 11 are folded by inward force applied thereto, the cardiac implantation device 1 may be placed in, for example, a compression sheath (referring to FIG. 11). Additionally, when received in the sheath, the cardiac implantation device 1 may appear like an umbrella or a bundle. That is, the compression sheath makes the N support struts 11 converge by elastically deforming them through applying forces on the support struts 11. This allows easier delivery of the entire cardiac implantation device 1 into the superior vena cava. When the cardiac implantation device 1 is released from the compression sheath, the forces applied to the N support struts 11 by the compression sheath will be removed, and the N support struts 11 will spontaneously radiate by its own elasticity. As a result, the anchors 111 of the N support struts 11 will abut against the inner wall of the superior vena cava, thus supporting and securing the cardiac implantation device 1 in the superior vena cava.

Compared with the prior art, the N support struts 11 according to this embodiment of the present invention will converge inwardly toward the axis of the first connecting member 10 when inward forces are applied thereto so that the cardiac implantation device 1 can be easily delivered into the superior vena cava until the leadless pacemaker 2 reaches a target site. When the leadless pacemaker 2 is delivered in place, the inward forces will be removed, followed by spontaneous expansion of the N support struts 11, which enables the leadless pacemaker 2 to be supported and secured in the superior vena cava. Therefore, the implantation device according to this embodiment of the present invention allows very easy implantation of the leadless pacemaker 2. Moreover, after long-term implantation, the leadless pacemaker 2 can be retrieved simply by applying inward forces to the N support struts 11, for example, through disposing the compression sheath over the cardiac implantation device 1, the inward forces is applied to the N support struts 11, so that the cardiac implantation device 1 can be entirely separated from the superior vena cava, that is, the cardiac implantation device 1 can be retrieved, thereby achieving retrieval of the leadless pacemaker 2. The retrieval can be achieved with a very high success rate because of simple and easy convergence of the cardiac implantation device 1 and easy separation of the cardiac implantation device 1 from the superior vena cava. Thus, the cardiac implantation device 1 according to this embodiment allows not only convenient and reliable implantation of the leadless pacemaker 2 into the superior vena cava for atrial sensing and pacing but also a higher long-term retrieval success rate, thus helping in promoting the application of leadless pacemakers 2.

A second embodiment of the present invention relates to a cardiac implantation device 1 in which the anchors 111 are of an alternative structure.

Figure 6:
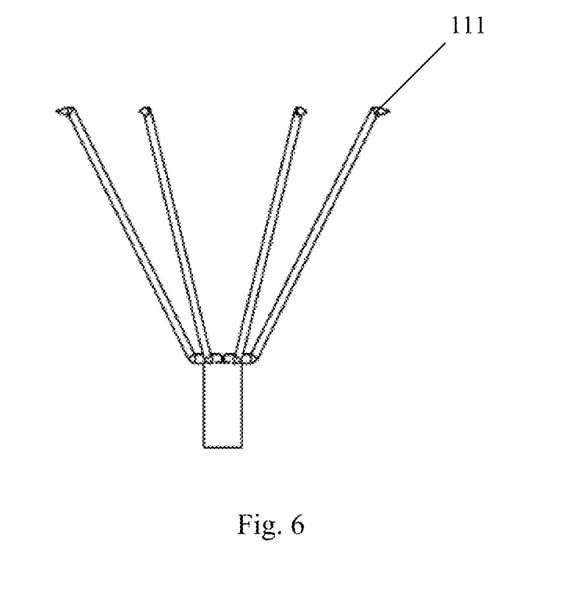
FIG. 6 is a schematic diagram illustrating the cardiac implantation device according to the second embodiment of the present invention in an unfolded configuration.
Figure 7:
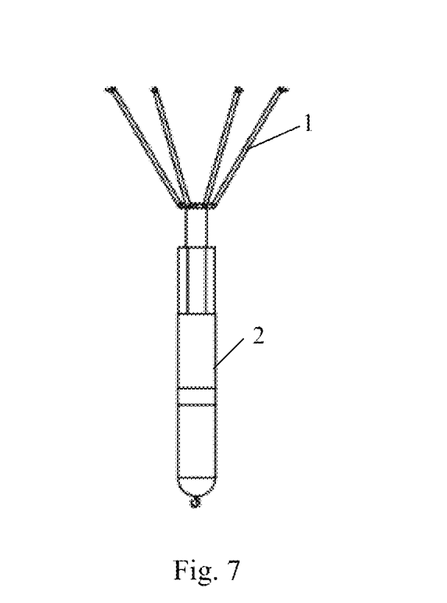
FIG. 7 schematically illustrates the coupling of the cardiac implantation device of FIG. 6 to a leadless pacemaker.

Referring to FIGS. 6 and 7, in this embodiment, the anchors 111 have a barb-like structure with sharp ends, which can pierce into the inner wall of the superior vena cava obliquely downward and thus provide the leadless pacemaker 2 with upward support. When inward forces are applied to the support struts 11, the anchors 111 implemented as barb-like structure can be smoothly retracted and separated from the superior vena cava, without imposing any adverse impact on the retrieval of the cardiac implantation device. This embodiment is not limited to any particular shape or size of the barbs.

Compared with those of the first embodiment, the barb-like anchors 111 according to second embodiment allow the cardiac implantation device 1 to be more reliably supported and secured to the wall of the superior vena cava and thus enable implantation of the leadless pacemaker 2 with a higher positional stability.

Figure 8:
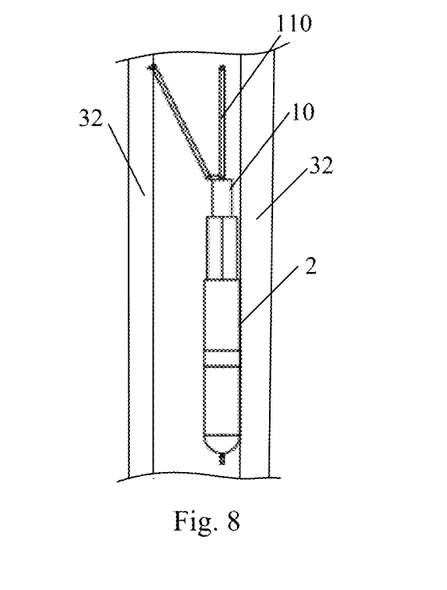
FIG. 8 is a schematic illustration of the cardiac implantation device of FIG. 6 that has been implanted.
Figure 9:
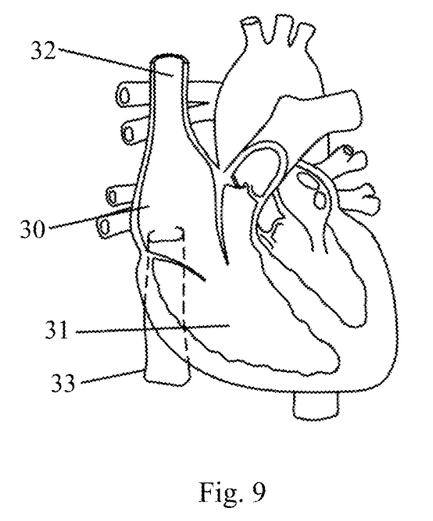
FIG. 9 is an anatomical schematic of the human heart.

Reference is now made to FIG. 9, an anatomical schematic of the human heart, illustrating the right atrium 30, the right ventricle 31, the superior vena cava 32 and the inferior vena cava 33. FIG. 8 is a structural schematic of the cardiac implantation device according to second embodiment that has been implanted in the superior vena cava. As shown, since the support struts 11 are secured to half circumference of the circular end of the first connecting member 10, when the leadless pacemaker 2 is implanted in the superior vena cava 32, the leadless pacemaker 2 is pressed against the inner wall of the superior vena cava 32 under the action of the abutment of the N support struts 11 against the same. This helps in atrial sensing and pacing of the leadless pacemaker.

Compared with that of the first embodiment, the leadless pacemaker of second embodiment allows more stable and more reliable positioning.

In embodiments of the present invention, there is also provided a cardiac pacing system including the implantation device as defined above and a pacemaker coupled to the implantation device. In another embodiment, the support struts of the implantation device are received in a positioning sheath prior to the implantation, the pacemaker is provided, at the other end (which is the proximal end not coupled to the cardiac implantation device), a pull hook configured for removal of a tether for the sheath during extraction of the cardiac implantation device.

An example of how the cardiac implantation device 1 according the foregoing embodiments is implanted and retrieved will be explained.

Figure 10:
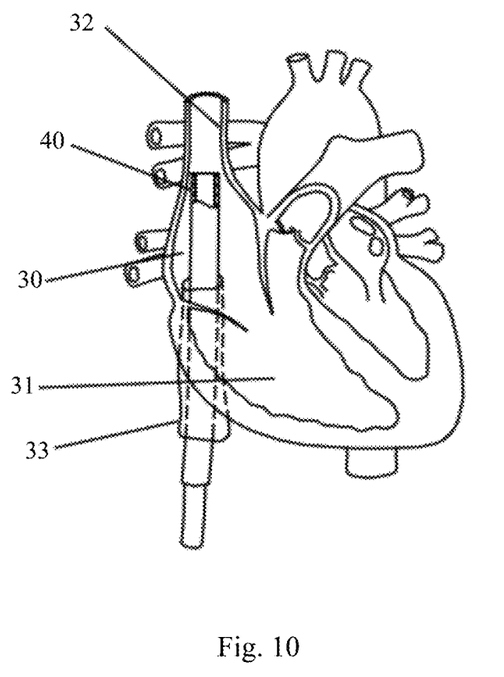
FIGS. 10 and 11 schematically illustrate the implantation of a cardiac implantation device according to an embodiment of the present invention.

The implantation of the leadless pacemaker 2 may be accomplished in the following steps:

referring to FIGS. 10 and 11, the surgeon may first introduce the guide sheath 40 through the femoral vein and the inferior vena cava 33, followed by slow delivery of the compression sheath 41 and the positioning sheath 42, in which the cardiac implantation device 1 and the leadless pacemaker 2 are loaded, to the patient's superior vena cava 32 through the guide sheath 40. After that, it may be determined whether the leadless pacemaker 2 has reached the target site by translating or rotating the compression sheath 41 under the guidance of X-ray imaging. Once the correct positioning has been repeatedly confirmed, the compression sheath 41 may be slowly retracted, resulting in the complete expansion and release of the cardiac implantation device 1 and hence securing of the leadless pacemaker 2 to the SVC wall by the cardiac implantation device 1, as shown in FIG. 8.

Figure 12:
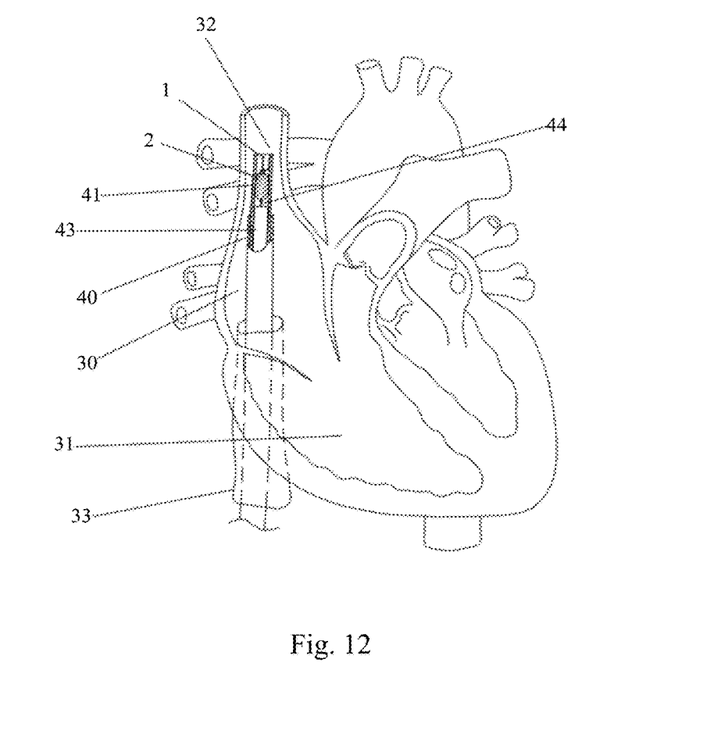
FIG. 12 schematically illustrates the retrieval of a cardiac implantation device according to an embodiment of the present invention.

The retrieval of the leadless pacemaker 2 after long-term implantation may be accomplished in the following steps:

referring to FIG. 12, the surgeon may first introduce the guide sheath 40 through the femoral vein and the inferior vena cava 33, followed by slow advancement of the compression sheath 41 and an extraction sheath 43 through the guide sheath 40 toward the leadless pacemaker 2 under the guidance of X-ray imaging. After that, the extraction sheath 43 and the tether 44 of the extraction sheath 43 may be slowly extended, and the tether 44 may be then secured to the pull hook of the leadless pacemaker 2. After securing the leadless pacemaker 2, the compression sheath 41 may be slowly advanced to the cardiac implantation device 1, concurrently with simultaneous retraction of the extraction sheath 43 and advancement of the compression sheath 41, until the cardiac implantation device 1 is received within the compression sheath 41. Thereafter, the extraction sheath 43 and the compression sheath 41 may be slowly withdrawn, followed by the final removal of the guide sheath 40.

It will be appreciated that the above description of the implantation and retrieval steps is merely illustrative and should not be construed as being limiting.

Those of ordinary skill in the art will appreciate that the foregoing embodiment are particular embodiments presented to enable practicing of the present invention. In practical applications, various changes can be made to their form and details without departing from the spirit and scope of the invention.

What is claimed is:

1. A cardiac implantation device, comprising:
a first connecting member having a proximal end configured to be coupled to a pacemaker; and
N support struts, each of the N support struts comprising an anchor and having a proximal end coupled to a distal end of the first connecting member, wherein: the anchor is configured to secure the pacemaker during implantation; and each of the support struts has a distal end that is free and is able to radiate outwardly or converge inwardly, where N is a natural number greater than or equal to 1;
wherein the anchor is arranged at a distal end of the support strut;
wherein N is greater than 1, and all the proximal ends of the N support struts are evenly arranged along half of a circumference of a distal end portion of the first connecting member, and nothing is provided at another half of the circumference of the distal end portion of the first connecting member, and
wherein the anchor has a barb-like structure.

2. The cardiac implantation device of claim 1, wherein the N support struts are coupled to the distal end of the first connecting member by welding or crimping.

3. The cardiac implantation device of claim 2, wherein the cardiac implantation device is made of a biocompatible metallic material, and wherein the N support struts are made of a biocompatible elastic metallic material.

4. A cardiac pacing system comprising a cardiac implantation device as defined in claim 1 and a pacemaker coupled to the cardiac implantation device.

5. The cardiac pacing system of claim 4, wherein the first connecting member of the cardiac implantation device is coupled, at the proximal end, to the pacemaker through a second connecting member.

6. The cardiac pacing system of claim 5, wherein each of the first and second connecting members has a cylinder-like structure, and the first and second connecting members are connectable with each other in a matching manner.

7. The cardiac pacing system of claim 6, wherein the second connecting member connects with the first connecting member in a matching manner by an internal or an external thread.

8. The cardiac pacing system of claim 4, wherein an end of the pacemaker that is not coupled to the cardiac implantation device is provided with a pull hook.

9. The cardiac pacing system of claim 4, wherein prior to implantation of the cardiac pacing system, the N support struts of the cardiac implantation device are received in a positioning sheath.

10. The cardiac implantation device of claim 1, wherein each of the N support struts further comprises a strut body which has a shape of straight line when the support strut radiates outwardly.

\* \* \* \* \*